United States Patent [19]

Tessier et al.

[11] Patent Number: 4,607,026

[45] Date of Patent: * Aug. 19, 1986

[54] CYCLOPROPANE THIOCARBOXYLIC ESTERS AND INSECTICIDAL AND ACARICIDAL USE THEREOF

[75] Inventors: Jean Tessier, Vincennes; André Teche, Paris, both of France

[73] Assignee: Roussel Uclaf, Paris, France

[*] Notice: The portion of the term of this patent subsequent to Dec. 18, 2001 has been disclaimed.

[21] Appl. No.: 427,887

[22] Filed: Sep. 29, 1982

[30] Foreign Application Priority Data

Oct. 16, 1981 [FR] France .................................. 81 19481

[51] Int. Cl.⁴ ...................... A01N 43/08; A01N 43/36; C07D 233/30; C07C 153/023
[52] U.S. Cl. ....................................... 514/80; 546/270; 514/89; 548/465; 548/479; 514/94; 548/309; 548/312; 514/99; 548/127; 548/128; 514/112; 548/134; 548/136; 514/114; 548/214; 548/236; 514/119; 514/125; 514/128; 514/130; 514/134; 514/336; 514/345; 514/389; 514/414; 514/417; 514/451; 514/459; 514/461; 514/467; 514/471; 514/513; 558/255; 549/435; 549/447; 549/448; 549/454; 549/414; 549/420; 549/473; 549/500; 546/283; 546/301

[58] Field of Search ................... 260/455 R; 558/255; 542/427; 424/285, 274, 263, 301; 549/435, 447, 448, 454, 414, 420, 473, 500; 546/283, 301, 270; 548/465, 479, 309, 312, 127, 128, 134, 136, 214, 236; 514/80, 89, 94, 99, 112, 114, 119, 125, 128, 130, 134, 336, 345, 389, 414, 417, 451, 459, 461, 467, 471, 513

[56] References Cited

U.S. PATENT DOCUMENTS

| | | | |
|---|---|---|---|
| 4,051,104 | 9/1977 | Spivack et al. | 260/455 R |
| 4,230,722 | 10/1980 | Malherbe et al. | 260/455 R |
| 4,231,953 | 11/1980 | Henrick et al. | 260/455 R |
| 4,489,093 | 12/1984 | Martel et al. | 546/300 |

FOREIGN PATENT DOCUMENTS 2486073 1/1982 France ................................. 546/300

Primary Examiner—Henry R. Jiles
Assistant Examiner—Robert C. Whittenbaugh
Attorney, Agent, or Firm—Bierman, Peroff & Muserlian

[57] ABSTRACT

This invention relates to stereoisomeric forms and mixtures thereof of compounds of the formula

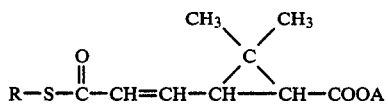

having insecticidal, nematocidal, and acaricidal properties.

29 Claims, No Drawings

CYCLOPROPANE THIOCARBOXYLIC ESTERS AND INSECTICIDAL AND ACARICIDAL USE THEREOF

STATE OF THE ART

Certain derivatives of cyclopropane carboxylic acid derivatives are known having in the 3-position the group ROOC—CH=CH— having essentially E geometry. Examples of such prior art are French Pat. No. 2,185,612 as well as J. Chem. Soc., Perkin I (1974), p. 2470 and Pest. Sci., Vol. 7 (1976), p. 499. The processes used to prepare these derivatives lead almost exclusively to the E geometry (for example Arg. Biol. Chem. Vol. 34 (1970), p. 1119). Furthermore, for those compounds with the side chain geometry in the E state, it has not been possible to make evident any remarkable properties. The French Pat. Nos. 2,418,218 and 2,143,820 also describe compounds substituted in the 3-position by the group ROOC—CH=CH—.

Also related are commonly assigned U.S. patent applications Ser. No. 254,537 filed Apr. 15, 1981, Ser. No. 266,164 filed May 22, 1981 and Ser. No. 279,076 filed June 30, 1981 with a different substituent in the 3-position.

OBJECTS OF THE INVENTION

It is an object of the invention to provide the novel Z and E isomers of the compounds of formula I as well as a novel process and novel intermediates for the preparation.

It is another object of the invention to provide novel pesticidal compositions and a novel method of killing insects, nematodes and vegetable and animal acariens.

It is a further object of the invention to provide novel compositions and method of combatting scabies and to provide anthelmintic activity.

These and other objects and advantages of the invention will become obvious from the following detailed description.

THE INVENTION

The novel compounds of the invention are the stereoisomeric forms and mixtures thereof of compounds of the formula

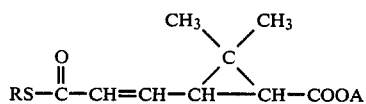

wherein R is selected from the group consisting of aryl of 6 to 14 carbon atoms optionally substituted, optionally unsaturated cycloalkyl of 3 to 7 carbon atoms optionally substituted, optionally substituted heterocycle and optionally unsaturated alkyl of 1 to 18 carbon atoms optionally substituted, A is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

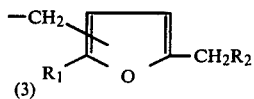

wherein $R_1$ is selected from the group consisting of hydrogen and methyl and $R_2$ is selected from the group consisting of —CH$_2$—C≡CH and monocyclic aryl,

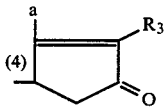

wherein a is selected from the group consisting of hydrogen and methyl and $R_3$ is an aliphatic group of 2 to 6 carbon atoms containing at least one carbon-carbon unsaturation,

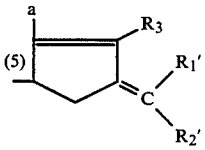

wherein a is selected from the group consisting of hydrogen and methyl and $R_3$ has the above definition and $R_1'$ and $R_2'$ are individually selected from the group consisting of hydrogen, halogen, alkyl of 1 to 6 carbon atoms, aryl of 6 to 10 carbon atoms, cyano and alkoxycarbonyl of 2 to 5 carbon atoms,

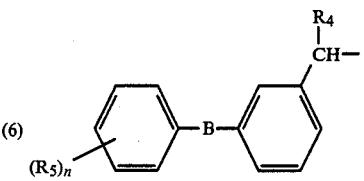

wherein B is selected from the group consisting of —CH$_2$—,

—O— and —S—, $R_4$ is selected from the group consisting of hydrogen, —CN, —CH$_3$, —CONH$_2$, —CSNH$_2$, and —C≡CH, $R_5$ is selected from the group consisting of halogen and —CH$_3$ and n is an integer from 0, 1 or 2

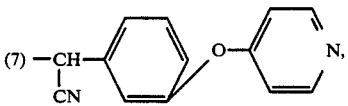

-continued

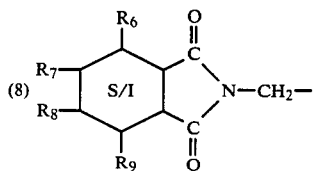

wherein $R_6$, $R_7$, $R_8$ and $R_9$ are selected from the group consisting of hydrogen, chlorine and methyl and S/I symbolizes an aromatic ring or dihydro or tetrahydro ring,

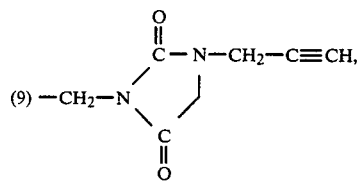

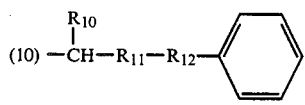

wherein $R_{10}$ is selected from the group consisting of hydrogen and —CN, $R_{12}$ is selected from the group consisting of —$CH_2$— and —O— and $R_{11}$ is selected from the group consisting of thiazolyl and thiadiazolyl with the bond to $$\overset{R_{10}}{\underset{|}{-CH-}}$$

being in one of the positions so that there is a carbon atom wherein $R_{11}$ and $R_{12}$ are connected between a sulfur atom and a nitrogen atom,

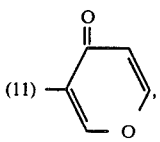

wherein $R_{13}$ is selected from the group consisting of hydrogen and —CN,

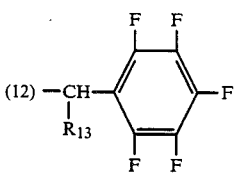

wherein $R_{13}$ has the above definition and the benzoyl is in the 4-position,

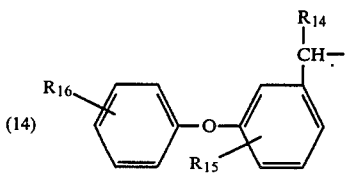

wherein $R_{14}$ is selected from group consisting of hydrogen, methyl, ethynyl and —CN and $R_{15}$ is selected from the group consisting of fluorine, chlorine and bromine and $R_{16}$ is selected from the group consisting of hydrogen, bromine, chlorine and fluorine and

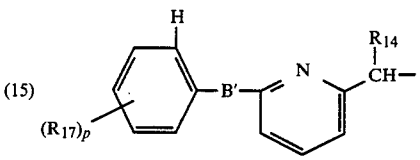

wherein $R_{14}$ has the above definition p is 0,1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —$CF_3$, 3,4-methylenedioxy, chlorine, bromine and fluorine, B' is selected from the group consisting of —O— and —S— and the double bond in the 1'-position of the 3-lateral side chain has Z or E geometry.

The compounds of formula I can exist in numerous stereoisomeric forms due to the presence of asymetric carbon atoms in the 1- and 3-positions of the cyclopropane ring and also have the Z and E isomeric forms due to the double bond. Moreover, the compounds of formula I can possess one or more other asymetric centers in the A substituent and the R substituent.

An example of $R_2$ as monocyclic aryl is 5-benzyl-3-furyl-methyl and examples of $R_3$ are —$CH_2$—CH=$CH_2$, —$CH_2$—CH=CH—$CH_3$, —$CH_2$—CH=CH—$CH_2$—$CH_3$ and —$CH_2$—CH=CH—CH=$CH_2$. Examples of substituent (6) are 3-phenoxy-benzyl, α-cyano-3-phenoxy-benzyl, α-ethynyl-3-phenoxy-benzyl, 3-benzoyl-benzyl, 1-(3-phenoxyphenyl)-ethyl and α-thioamido-3-phenoxy-benzyl.

Examples of A are alkyl such as methyl, ethyl, n-propyl, isopropyl, isobutyl, tert.-butyl and n-butyl; benzyl optionally substituted with at least one alkyl such as methyl or ethyl; benzyl optionally substituted with at least one alkenyl such as vinyl, allyl, 2-methylallyl and isobutenyl; and benzyl substituted with at least one alkenyloxy such as vinyloxy, allyloxy, 2-methylallyloxy and isobutenyloxy; and benzyl substituted with at least one halogen such as chlorine, bromine or fluorine.

$R_2$ is preferably phenyl and $R_3$ is preferably selected from the group consisting of —$CH_2$—CH=$CH_2$, —$CH_2$—CH=CH—$CH_3$, —$CH_2$—CH=CH—CH=$CH_2$ and —$CH_2$—CH=CH—$CH_2$—$CH_3$. $R_1'$ and $R_2'$ are preferably selected from the group consisting of fluorine, bromine, chlorine, methyl, ethyl, branched or straight chain hexyl, phenyl, methoxycarbonyl, ethoxycarbonyl or branched or straight chain pentoxycarbonyl. $R_5$ is preferably fluorine, chlorine or bromine and $R_{17}$ is preferably methyl, ethyl, branched or linear propyl or propoxy or propylthio, branched or linear butyl or butoxy or butylthio, methoxy, ethoxy, methylthio, ethylthio, methylsulfonyl, ethylsulfonyl or branched or linear propylsulfonyl or butylsulfonyl.

Examples of R as alkyl are methyl, ethyl, propyl, isopropyl and branched or straight chain butyl, pentyl, hexyl, decyl, tetradecyl or octadecyl. Examples of R as unsaturated alkyl are alkenyl such as ethenyl, propenyl and branched or linear butenyl, pentenyl, hexenyl, decenyl, tetradecenyl or octadecenyl or alkynyl such as ethynyl, propynyl and unsaturated aliphatic radicals having 2 or more double bonds.

Examples of R substituted with one or more functional groups are preferably alkyl of 1 to 8 carbon atoms such as methyl, ethyl, propyl, isopropyl, n-butyl, isobutyl, tert.-butyl and branched or linear octyl substituted with at least one member of the groups consisting of halogen, —OH, —SH, —OR' and —SR' and R' is selected from the group consisting of alkyl of 1 to 8 carbon atoms, —NO₂, —CN, —SO₃H, —PO₄H₂,

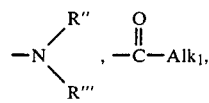

—SO₂Alk₂ and SO₃Alk₃, R" and R''' are individually selected from the group consisting of hydrogen and alkyl of 1 to 8 carbon atoms and Alk₁, Alk₂ and Alk₃ are alkyl of 1 to 18 carbon atoms.

R may also be alkyl substituted with an aryl group such as benzyl or phenethyl optionally substituted with at least one member of the group consisting of —OH, alkyl and alkoxy of 1 to 8 carbon atoms, halogens, —CF₃, —OCF₃, —SCF₃ and

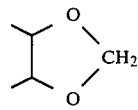

(G). R may also be alkyl substituted on two adjacent carbon atoms with the group

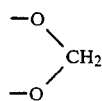

(G₁) or substituted with

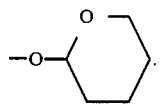

When R is an alkyl radical substituted by one or more functional groups, the preferred examples of R are (1) —(CH₂)ₙ—CHal₃ wherein n is an integer from 1 to 8 and Hal is a halogen, such as —CH₂—CCl₃, —CH₂—CF₃, —CH₂—CH₂—CCl₃ or —CH₂—CH₂—CF₃, (2) —(CH₂)ₙ₁—CHHal₂ wherein n₁ is 0 to 8 and Hal is halogen such as —CH₂—CHCl₂, —CH₂—CHF₂ and —CHF₂, (3) —(CH₂)ₙ—CH₂Hal wherein Hal and n have the above definitions, such as —CH₂—CH₂—Cl or —CH₂—CH₂F, (4) —C—(CHal₃)₃ wherein Hal is a halogen such as —C(CF₃)₃ or

(5) 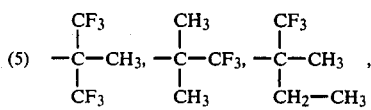

(6) 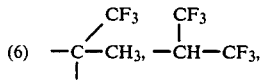

(7) 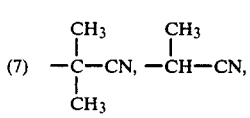

—(CH₂)ₙ—CN wherein n is 1 to 8, (8) 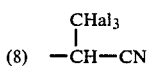

wherein Hal is halogen, such as

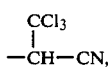

(CH₂)ₙ—OR' wherein n has the above definition and R' is hydrogen or branched or linear alkyl of 1 to 8 carbon atoms such as —CH₂—OCH₃, —CH₂—CH₂—OCH₃, —CH₂—CH₂—O—CH₂—CH₃ or —CH₂—CH₂—OH,

(10) 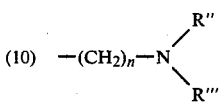

wherein n is 1 to 8 and R" and R''' are individually hydrogen or branched or linear alkyl of 1 to 8 carbon atoms such as —CH₂—CH₂—NH—CH₃,

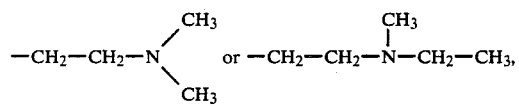

(11) 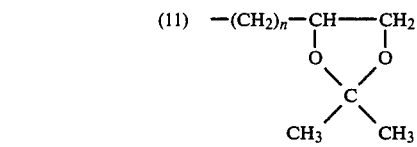

wherein n is 1 to 8 such as

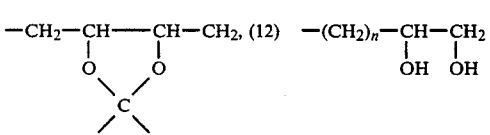

wherein n is 1 to 8 such as

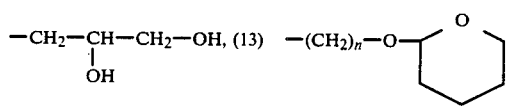

wherein n is 1 to 8 such as

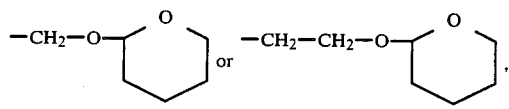

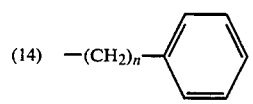

wherein n is 1 to 8 such as benzyl or phenethyl and

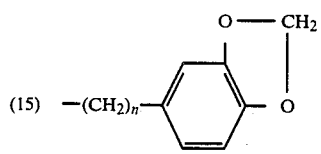

wherein n is 1 to 8 such as

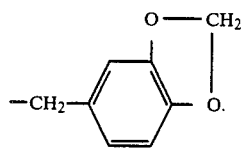

Examples of R are saturated or unsaturated cycloalkyl or cycloalkylalkyl of 3 to 7 carbon atoms such as cyclopropyl, cyclobutyl, cyclopentyl, cyclohexyl, cycloheptyl, cyclopropylmethyl, 1-cyclopropylethyl, optionally substituted on the cycloalkyl with at least one member of the group consisting of halogen, alkyl of 1 to 6 carbon atoms, alkoxy of 1 to 6 carbon atoms and $-NO_2$.

Examples of R are also 1-methyl-cyclobutyl, 1-methyl-cyclopentyl, 1-methyl-cyclohexyl and 2,2,3,3-tetramethyl-cyclopropyl.

When R is an optionally substituted aryl, preferred examples are phenyl optionally substituted with at least one member of the group consisting of —OH, alkyl and alkoxy of 1 to 8 carbon atoms, $-CF_3$, $-OCF_3$, $-SCH_3$/Cl, Br and F. Examples of R as heterocycles are pyridinyl, furanyl, thiophenyl, oxazolyl and thiazolyl.

The preferred compounds of formula I have the cyclopropanecarboxylic acid in the 1R, cis or 1R, trans structure and most preferably have the 1R, cis structure. The preferred compounds of formula I have the double bond with the geometry Z.

Among the preferred compounds of formula I are those wherein A is (R), (RS) or (S)α-cyano-3-phenoxybenzyl, those wherein A is [3-(propyn-2-yl)-2,5-dioxoimidazolidinyl]-methyl and those wherein R is alkyl of 1 to 18 carbon atoms, especially methyl, ethyl, isopropyl and tert.-butyl.

The novel process of the invention for the preparation of a compound of formula I comprises reacting an acid of the formula

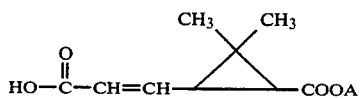

wherein A has the above definition in an organic solvent in the presence of dicyclohexylcarbodiimide with a mercaptan of the formula

R—SH    III wherein R has the above definition. The organic solvent is preferably methylene chloride, benzene or tetrahydrofuran.

If the reactant RSH possesses other functional groups which could react with the acid of formula II, the said groups would have to be blocked before the condensation by known methods. Preferably, the reaction is effected in the further presence of 4-dimethylaminopyridine.

The novel pesticidal compositions of the invention are comprised of a pesticidally effective amount of at least one compound of formula I and an inert carrier. The compositions are useful to combat pests such as parasites of vegetables and of warm-blooded animals as well as domestic parasites and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The products of formula I have the advantages of being very photostable and not being toxic to mammals. The various properties of the compounds of formula I correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as saracoptic scabies, psoroptic scabies and chorioptic scabies.

The invention also includes compositions intended to combat parasites of warm-blooded animals, parasites of premises and parasites of vegetables containing at least one compound of formula I.

The invention particularly includes insecticidal compositions containing as active principle, at least one compound of formula I.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be also prepared as a spraying oil containing the active ingredient and the oil may soak the wick of a lamp which is then subjected to combustion. The concentration of the compound of formula I in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)-bicyclo-[2,2-1]5-heptene-2,3-dicarboximide or piperonyl-bis-2-(2'n-butoxy-ethoxy)-ethyl acetal (tropital).

When the compositions are to be used to combat parasitic acariens of animals, the active compounds of formula I are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meals of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropylacetic acids, esters of allethrolone,3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compound of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I.

The acids of formula II may be prepared by the processes described in published European patent applications No. 38,271, No. 41,021 and No. 48,186.

In the following examples there are described several preferred embodiments to illustrate the invention. However, it should be understood that the invention is not intended to be limited to the specific embodiments.

EXAMPLE 1

(S) α-cyano-3-phenoxy-benzyl (1R,cis) 2,2-dimethyl-3-[(ΔZ)-3-oxo-3-methylthio-propenyl]-cyclopropane-carboxylate and (S) α-cyano-3-phenoxy-benzyl (1R,cis) 2,2-dimethyl-3-[(ΔE)-3-oxo-3-methylthio-propenyl]-cyclopropane-carboxylate 2.16 g of dicyclohexylcarbodiimide were added at 0° C. to a mixture of 4.1 g of (S) α-cyano-3-phenoxy-benzyl (1R,cis) 2,2-dimethyl-3-[(ΔZ) 2-carboxyethenyl]-cyclopropanecarboxylate [described in EPC published application No. 38,271], 50 mg of 4-dimethylaminopyridine and 20 ml of methylene chloride and after stirring the mixture 5 minutes, a solution of 545 mg of methylmercaptan in 5 ml of benzene was added thereto all at once. The mixture was stirred at 0° C. for 5 minutes, then at 20° C. for 16 hours and was filtered. The filtrate was washed with aqueous N hydrochloric acid solution, and with water and was evaporated to dryness under reduced pressure. The residue was chromatographed over silica gel and was eluted with a 9-1 cyclohexane-ethyl acetate mixture to obtain 1.2 g of (S) α-cyano-3-phenoxy-benzyl (1R,cis) 2,2-dimethyl-3-[(ΔZ) 3-oxo-3-methylthio-propenyl]-cyclopropane-carboxylate with a melting point of 87° C. and a specific rotation of $[\alpha]_D^{20} = +51°$ (c=1% in benzene) and then 1.3 g of (S) α-cyano-3-phenoxy-benzyl (1R,cis) 2,2-dimethyl-3-[(ΔE)-3-oxo-3-methylthio-propenyl]-cyclopropane-carboxylate having a specific rotation of $[\alpha]_D^{20} = +67.5°$ (c=0.6% in benzene).

NMR Spectrum (deuterochloroform)

Z isomer—peaks at 1.25–1.27 ppm (hydrogens of geminal methyls); at 1.93–2.07 ppm (1-hydrogen of cyclopropane); at 2.38 ppm (hydrogens of $CH_3$—S—); at 3.2–3.5 ppm (3-hydrogen of cyclopropane); at 6.1–6.6 ppm (ethylenic hydrogens); at 6.4 ppm (hydrogen on carbon α- to —CN); at 7.0–7.6 ppm (aromatic hydrogens).

E isomer—peaks at 1.25–1.28 ppm (hydrogens of geminal methyls); at 1.9–2.1 ppm (1- and 3-hydrogens of cyclopropane); at 2.4 ppm (hydrogens of $CH_3$—S—); at 6.2–6.5 ppm and 7.0–7.2 ppm (ethylenic hydrogens); at 6.5 ppm (hydrogen on carbon α- to —CN); at 7.0 to 7.7 ppm (aromatic hydrogens).

EXAMPLE 2

(S) α-cyano-3-phenoxy-benzyl (1R,cis) 2,2-dimethyl-3-[(ΔZ)-3-oxo-3-ethylthio-propenyl]-cyclopropane-carboxylate 1.5 ml of ethane thiol were added all at once to a mixture of 2 g of (S) α-cyano-3-phenoxy-benzyl (1R,cis) 2,2-dimethyl-3-[(ΔZ)-carboxyethenyl]-cyclopropane-carboxylate in 10 ml of methylene chloride and then a solution of 1 g of dicyclohexylcarbodiimide, 40 mg of 4-dimethylamino-pyridine and 5 ml of methylene chloride was added thereto at 5° C. The mixture was stirred at 5° C. for 5 minutes and at room temperature for 3 hours. The mixture was filtered and the filtrate was evaporated to dryness under reduced pressure. The residue was chromatographed over silica gel and was eluted with an 8-2 n-hexane-ethyl acetate mixture to obtain 1.2 g of (S) α-cyano-3-phenoxy-benzyl (1R,cis) 2,2-dimethyl-3-[(ΔZ) 3-oxo-3-ethylthio-propenyl]-cyclopropane-carboxylate melting at 47° C. and having a specific rotation of $[\alpha]_D^{20} = +59°$ (c=0.4% in chloroform).

NMR Spectrum (deuterochloroform)

Peaks at 1.25–1.27 ppm (hydrogens of geminal methyls); at 1.23-1.31-1.39 ppm, 2.8–2.9 ppm and 3.0–3.1 ppm (hydrogens of $CH_3$—$CH_2$—S); at 1.95–2.04 ppm (1-hydrogen of cyclopropane); at 3.2–3.5 ppm (3-hydrogen of cyclopropane); at 6.2–6.5 ppm (ethylenic hydrogens); at 7.0–7.6 ppm (aromatic hydrogens).

EXAMPLE 3

(S) α-cyano-3-phenoxy-benzyl (1R,cis) 2,2-dimethyl-3-[(ΔZ) 3-oxo-3-isopropylthio-propenyl]-cyclopropane-carboxylate and (S) α-cyano-3-phenoxy-benzyl (1R,cis) 2,2-dimethyl-3-[(ΔE) 3-oxo-3-isopropylthio-propenyl]-cyclopropane-carboxylate 3 ml of 2-propanethiol were added all at once to a solution of 3.9 g of (S) α-cyano-3-phenoxy-benzyl (1R,cis) 2,2-dimethyl-3-[(ΔZ) carboxyethenyl]-cyclopropane-carboxylate in 25 ml of methylene chloride and then a solution of 2 g of dicyclohexylcarbodiimide and 70 mg of 4-dimethylamino-pyridine in 10 ml of methylene chloride were added at 5° C. to the mixture. The mixture was stirred at 5° C. for 5 minutes and then at room temperature for 3 hours and was filtered. The filtrate was evaporated to dryness under reduced pressure and the residue was chromatographed over silica gel. Elution with an 85-15 n-hexane-ethyl acetate mixture yielded 3.1 g of (S) α-cyano-3-phenoxy-benzyl (1R,cis) 2,2-dimethyl-3-[(ΔZ) 3-oxo-3-isopropylthio-propenyl]-cyclopropane-carboxylate melting at 80° C. and having a specific rotation of $[\alpha]_D^{20} = +69°$ (c=0.5% in chloroform) and then 340 mg of the corresponding E isomer melting at 87° C. and having a specific rotation of $[\alpha]_D^{20} = -6.5°$ (c=0.5% in chloroform).

NMR Spectrum (deuterochloroform)

Z isomer: Peaks at 1.27–1.28 ppm (hydrogens of geminal methyls); at 1.3–1.4 ppm (hydrogens of methyls of isopropyl); at 1.92–2.06 ppm (1-hydrogen of cyclopropyl); at 3.2–3.5 ppm (3-hydrogen of cyclopropyl); at 3.7 ppm (hydrogen of

of isopropyl); at 6.1 to 6.6 ppm (ethylenic hydrogens); at 6.4 ppm (hydrogen of carbon α to —CN); at 7.0–7.6 ppm (aromatic hydrogens).

E isomer: Peaks at 1.25–1.29 ppm (hydrogens of geminal methyls); at 1.29–1.4 ppm (hydrogens of methyls of isopropyl); at 1.95–2.16 ppm (1- and 3-hydrogens of cyclopropyl); at 3.7 ppm (hydrogen of

of isopropyl); at 6.18–6.4 ppm (ethyleneic hydrogen α- to

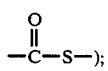

at 6.5 ppm (hydrogen of carbon α- to —CN); at 7. to 7.7 ppm (other ethylenic hydrogen); at 7 to 7.7 ppm (other ethylenic hydrogen); at 7 to 7.7 ppm (aromatic hydrogens).

EXAMPLE 4

(S) α-cyano-3-phenoxy-benzyl (1R,cis) 2,2-dimethyl-3-[(ΔZ) 3-oxo-3-tert.butylthio-propenyl]-cyclopropane-carboxylate and (S) α-cyano-3-phenoxy-benzyl (1R,cis) 2,2-dimethyl-3-[(ΔE) 3-oxo-3-tert.-butylthio-propenyl]-cyclopropane-carboxylate 150 mg of 4-dimethylamino-pyridine and 1.9 g of dicyclohexylcarbodiimide were added at 5° C. to a solution of 3.46 g of (S) α-cyano-3-phenoxy-benzyl (1R,cis) 2,2-dimethyl-3-[(ΔZ) carboxyethenyl]-cyclopropane-carboxylate in 20 ml of methylene chloride and the mixture was stirred for 5 minutes at 5° C. after which 5 ml of tert.-butylmercaptan were added thereto. The mixture was stirred at 5° C. and at 20° C. for 3 hours and was filtered. The filtrate was evaporated to dryness under reduced pressure and the residue was chromatographed over silica gel. Elution with a 9-1 cyclohexane-ethyl acetate mixture yielded 1.4 g of (S) α-cyano-3-phenoxy-benzyl (1R,cis) 2,2-dimethyl-3-[(ΔZ) 3-oxo-3-tert.-butylthio-propenyl]-cyclopropane-carboxylate melting at 76° C. and having a specific rotation of $[\alpha]_D^{20} + 55°$ (c=0.5% in benzene) and then 1.6 g of the E isomer melting at 95° C. and having a specific rotation of $[\alpha]_D^{20} = +62°$ (c=1% in benzene).

NMR Spectrum (deuterochloroform)

Z isomer: Peaks at 1.25–1.28 ppm (hydrogens of geminal methyls); at 1.5 ppm (hydrogens of tert.-butyl); at 1.9–2.1 ppm (1-hydrogen of cyclopropane); at 3.2–3.4 ppm (3-hydrogen of cyclopropane); at 6.0–6.6 ppm (ethylenic hydrogens); at 6.4 ppm (hydrogen on carbon α to ~CN); at 7.0–7.7 ppm (aromatic hydrogens).

E isomer: Peaks at 1.25–1.30 ppm (hydrogens of geminal methyls); at 1.5 ppm (hydrogens of tert.-butyl); at 1.8–2.2 ppm (1- and 3-hydrogens of cyclopropane); at 6.2–6.4 ppm (ethylenic hydrogen α to

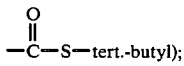

at 6.5 ppm (hydrogen of carbon α to —CN); at 6.9 to 7.7 ppm (aromatic hydrogens and other ethylenic hydrogen).

EXAMPLE 5

3-propyn-2-yl)-2,5-dioxo-imidazolidinylmethyl (1R,cis) 2,2-dimethyl-3-[ΔZ 3-oxo-3-thiomethyl-propenyl]-cyclopropane-carboxylate

STEP A:

3-(propyn-2-yl)-2,5-dioxo-imidazolidinylmethyl (1R,cis) 2,2-dimethyl-3[ΔZ carboxyethenyl]-cyclopropane-carboxylate 300 mg of p-toluene sulfonic acid monohydrate were added to a solution of 3.7 g of 1-[3-(propyn-2-yl)-2,5-dioxo-imidazolidinylmethyl] (1R,cis) 2,2-dimethyl-3-[(ΔZ) 3-oxo-3-tert.-butoxy-propenyl]-cyclopropane-carboxylate (described in published European patent application No. 41,021) in 35 ml of toluene and the mixture was refluxed until gas evolution ceased and was cooled to 0° C. The mixture was filtered and the filtrate was evaporated to dryness under reduced pressure. The residue was chromatographed over silica gel and eluted with a 60-40-1 hexane-ethyl acetate-acetic acid mixture to obtain 3.1 g of 3-(propyn-2-yl)-2,5-dioxoimidazolidinylmethyl (1R,cis) 2,2-dimethyl-3-[ΔZ 3-oxo-3-thiomethyl-propenyl]-cyclopropane-carboxylate with a specific rotation of $[\alpha]_D^{20} = +16°$ (c=0.25% in chloroform).

STEP B:

3-(propyn-2-yl)-2,5-dioxo-imidazolidinylmethyl (1R,cis) 2,2-dimethyl-3-[(ΔZ) 3-oxo-3-thiomethyl-propenyl]-cyclopropane-carboxylate A solution of 2.2 g of methyl mercaptan in 5 ml of methylene chloride was added to a solution of 2.3 g of the product of Step A in 5 ml of methylene chloride and then a solution of 1.45 g of dicyclohexyl-carbodiimide and 40 mg of 4-dimethylamino-pyridine in 5 ml of methylene chloride was added to the mixture at 5° C. The mixture was stirred at 5° C. for 5 minutes and at room temperature for 3 hours and was then filtered. The filtrate was evaporated to dryness under reduced pressure and the residue was chromatographed over silica gel. Elution with a 65-35 n-hexane-ethyl acetate mixture yielded 2.3 g of 3-(propyn-2-yl)-2,5-dioxo-imidazolidinylmethyl (1R,cis) 2,2-dimethyl-3[(ΔZ) 3-oxo-3-thiomethylpropenyl]-cyclopropane-carboxylate with a specific rotation of $[\alpha]_D^{20} = +17°$ (c=0.5% in CHCl₃).

NMR Spectrum (deuterochloroform)

Peaks at 1.26–1.30 ppm (hydrogens of geminal methyls); at 1.8–2.0 ppm (1-hydrogen of cyclopropane); at 2.33–2.37–2.42 ppm (hydrogen of ethynyl); at 2.35 ppm (hydrogens of —SCH₃); at 3.1–3.4 ppm (3-hydrogen of cyclopropane); at 4.0 ppm (4- hydrogen of imidazolidinyl); at 4.25–4.29 ppm (hydrogens of —CH₂— of propynyl α to imidazolidinyl); at 5.3–5.5 ppm and 5.5–5.7 ppm (hydrogens of —CH₂— α to

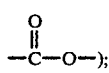

at 6.1–6.3 ppm (ethylenic hydrogen α to

and 6.2–6.6 ppm (other ethylenic hydrogen).

EXAMPLE 6

3-(propyn-2-yl)-2,5-dioxo-imidazolidinylmethyl (1R,cis) 2,2-dimethyl-3-[(ΔZ) 3-oxo-3-ethylthio-propenyl]-cyclopropane-carboxylate Using the procedure of Example 5, 2.1 g of the product of Step A of Example 5 and ethylmercaptan were reacted to obtain after chromatography over silica gel and elution with a 6-4 n-hexane-ethyl acetate mixture 1.57 g of 3-(propyn-2-yl)-2,5-dioxo-imidazolidinylmethyl (1R,cis) 2,2-dimethyl-3-[(ΔZ) 3-oxo-3-ethylthio-propenyl]-cyclopropane-carboxylate with a specific rotation of $[\alpha]_D^{20} = +19.5°$ (c=0.5% in CHCl₃).

NMR Spectrum (deuterochloroform)

Peaks at 1.26–1.30 ppm (hydrogens of geminal methyls); at 1.18 1.30–1.42 ppm (hydrogens of —S—CH₂—CH₃); at 1.84–1.98 ppm (1-hydrogen of cyclopropane); at 2.34-2.38-2.42 ppm (hydrogen of C≡CH); at 3.13-3.4 ppm (3-hydrogen of cyclopropane); at 4.0 ppm (4-hydrogens of pyridimidinyl); at 4.30-4.32 ppm (hydrogens of —CH$_2$— α to ethenyl); at 5.6 ppm (hydrogens α to

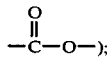

at 6.1-6.6 ppm (other ethylenic hydrogen).

EXAMPLE 7

3-(propyn-2-yl)-2,5-dioxo-imidazolidinylmethyl (1R,cis) 2,2-dimethyl-3-[(ΔZ) 3-oxo-3-isopropylthio-propenyl]-cyclopropanecarboxylate Using the procedure of Example 5, 1 g of the product of Step A of Example 5 and 2-propanethiol were reacted to obtain after chromatography over silica gel and elution with a 7-3 n-hexane-ethyl acetate mixture 750 mg of 3-(propyn-2-yl)-2,5-dioxo-imidazolidinylmethyl (1R,cis) 2,2-dimethyl-3-[(ΔZ) 3-oxo-3-isopropylthio-propenyl]-cyclopropane-carboxylate with a specific rotation of $[\alpha]_D^{20} = +28°$ (c=0.4% in CHCl$_3$).

NMR Spectrum (deuterochloroform)

Peaks at 1.26-1.28 ppm (hydrogens of geminal methyls); at 1.3-1.4 ppm (hydrogens of methyls of isopropyl); at 1.8-2.0 ppm (1-hydrogen or cyclopropane); at 2.31-2.36-2.40 ppm (hydrogen of —C≡CH); at 3.1-3.4 ppm (3-hydrogen of cyclopropane); at 3.7 ppm (hydrogen of

of isopropyl); at 4.0 ppm (hydrogens of 4-methylene of imidazolidinyl; at 4.25-4.29 ppm (hydrogens of —CH$_2$— α to —C≡CH; at 5.5 ppm (hydrogens of —CH$_2$— α to

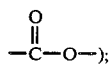

at 6.0-6.2 ppm (ethylenic hydrogen α to

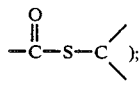

at 6.2-6.6 ppm (other ethylenic hydrogen).

EXAMPLE 8

ΔZ and ΔE isomers of 3-(propyn-2-yl)-2,5-dioxo-imidazolidinylmethyl (1R,cis) 2,2-dimethyl-3-(3-oxo-3-tert.-butylthiopropenyl)-cyclopropane-carboxylate Using the procedure of Example 5, 1.65 g of the product of Step A of Example 5 and tert.-butyl mercaptan were reacted to obtain after chromatography over silica gel and elution with a 6-4 n-hexane-ethyl acetate mixture and then a 7-3 n-hexane-ethyl acetate mixture 900 mg of the Z isomer of 3-(propyn-2-yl)-2,5-dioxo-imidazolidinylmethyl (1R,cis) 2,2-dimethyl-3-(3-oxo-3-tert.-butylthio-propenyl)-cyclopropane-carboxylate with a specific rotation of $[\alpha]_D^{20} = +46.5°$ (c=0.5% in chloroform) and then 900 mg of of E isomer of 3-(propyn-2-yl)-2,5-dioxo-imidazolidinylmethyl (1R,cis) 2,2-dimethyl-3-(3-oxo-3-tert.-butylthio-propenyl)-cyclopropane-carboxylate with a specific rotation of $[\alpha]_D^{20} = -74.5°$ (c=0.5% in chloroform).

NMR Spectrum (deuterochloroform)

Z isomer: Peaks at 1.27-1.32 ppm (hydrogens of geminal methyls); at 1.5 ppm (hydrogens of tert.-butyl); at 1.83-1.97 ppm (1-hydrogen of cyclopropane); at 2.32-2.35-2.40 ppm (hydrogen of —C≡CH); at 3.12-3.4 ppm (3-hydrogen of cyclopropane); at 4.05 ppm (hydrogens of 4-methylene of imidazolidinyl); at 4.25-4.29 ppm (hydrogens of —CH$_2$— α to ethynyl); at 5.5 ppm (hydrogens of —CH$_2$— α to

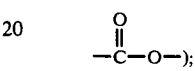

at 5.9-6.1 ppm (ethylenic hydrogen α to

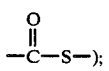

at 6.1-6.5 ppm (other ethylenic hydrogen).

E isomer: Peaks at 1.22-1.34 ppm (hydrogens of geminal methyls); at 1.5 ppm (hydrogens of tert.-butyl); at 1.67-2.0 ppm (1- and 3-hydrogens of cyclopropane); at 2.32-2.37-2.41 ppm (hydrogen of —C≡CH); at 4.05 ppm hydrogens of 4-methylene of imidazolidinyl); at 4.25-4.29 ppm (hydrogens of —CH$_2$— α to ethynyl); at 5.36-5.52 ppm and 5.53-5.68 ppm (hydrogens of —CH$_2$— α to

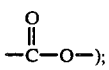

at 6.0-6.3 ppm (hydrogen α to

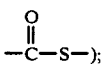

at 6.8-7.3 ppm (other ethylenic hydrogen).

EXAMPLE 9

Z and E isomers of (R,S) cyano-2-(6-phenoxypyridyl)-methyl (1R,cis) 2,2-dimethyl-3-(3-oxo-3-isopropylthio-propenyl)-cyclopropane-carboxylate Using the procedure of Example 5, 4.1 g of (R,S) cyano-2-(6-phenoxypyridyl)-methyl (1R,cis) 2,2-dimethyl-3-[(ΔZ) carboxyethenyl]-cyclopropane-carboxylate [free acid described in European application No. 41,021] and isopropylmercaptan were reacted to obtain after chromatography over silica gel and elution with methylene chloride 1.9 g of the Z isomer of (R,S) cyano-2-(6-phenoxypyridyl)-methyl (1R,cis) 2,2-dimethyl-3-(3-oxo-3-isopropylthio-propenyl)-cyclopropane-carboxylate with a specific rotation of $[\alpha]_D^{20} = +61.5° \pm 2.5°$ (c=0.5% in benzene) and then 1.2 g of E isomer with a specific rotation of $-45°$ (c=0.25% in benzene).

| Analysis: $C_{25}H_{26}N_2O_4S$; molecular weight = 450.561 | | | | |
|---|---|---|---|---|
| Calculated: | % C 66.65 | % H 5.82 | % N 6.22 | % S 7.12 |
| Found: Z isomer | 66.7 | 5.9 | 6.2 | 7.0 |
| E isomer | 66.3 | 5.8 | 6.1 | 7.2 |

EXAMPLE 10

Z and E isomers of (R,S) cyano-2-(6-phenoxypyridyl)-methyl (1R,cis) 2,2-dimethyl-3-[3-oxo-3-tert.-butylthio-propenyl]-cyclopropane-carboxylate Using the procedure of Example 9, (R,S) cyano-2-(6-phenoxypyridyl)-methyl (1R,cis) 2,2-dimethyl-3-[(ΔZ) carboxyethenyl]-cyclopropane-carboxylate derived from 4 g of the acid and tert.-butylmercaptan were reacted to obtain 1.5 g of the Z isomer of (R,S) cyano-2-(6-phenoxypyridyl)-methyl (1R,cis) 2,2-dimethyl-3-[3-oxo-3-tert.-butylthio-propenyl]-cyclopropane-carboxylate with a specific rotation of $[\alpha]_D^{20} = +71.5° \pm 3°$ (c=0.5% in benzene) and 1.8 g of E isomer with a specific rotation of $[\alpha]_D^{20} = -41° \pm 2°$ (c=0.9% in benzene).

| Analysis $C_{26}H_{28}N_2O_4S$; molecular weight = 464.588 | | | | |
|---|---|---|---|---|
| Calculated: | % C 67.22 | % H 6.08 | % N 6.03 | % S 6.90 |
| Found: Z isomer | 66.9 | 6.0 | 5.9 | 6.9 |
| E isomer | 66.2 | 6.1 | 5.8 | 6.5 |

EXAMPLE 11

Z and E isomers of (R,S) cyano-2-(6-phenoxypyridyl)-methyl (1R,cis) 2,2-dimethyl-3-[3-oxo-3-ethylthio-propenyl]-cyclopropane-carboxylate Using the procedure of Example 9, (R,S) cyano-2-(6-phenoxypyridyl)-methyl (1R,cis) 2,2-dimethyl-3-[(ΔZ) carboxyethenyl]-cyclopropane-carboxylate derived from 4 g of the free acid and ethylmercaptan were reacted to obtain 2.62 g of the Z isomer of (R,S) cyano-2-(6-phenoxy pyridyl)-methyl (1R,cis) 2,2-dimethyl-3-[3-oxo-3-ethylthiopropenyl]-cyclopropane-carboxylate with a specific rotation of $[\alpha]_D^{20} = +94.5° \pm 2.5°$ (c=1% in chloroform) and then 0.64 g of the E isomer with a specific rotation of $[\alpha]_D^{20} = -58° \pm 2.5°$ (c=0.5% in CHCl₃).

| Analysis: $C_{25}H_{25}N_2O_4S$; molecular weight = 436.534 | | | | |
|---|---|---|---|---|
| Calculated: | % C 66.04 | % H 5.54 | % N 6.42 | % S 7.34 |
| Found: Z isomer | 66.3 | 5.6 | 6.1 | 7.6 |
| E isomer | 66.0 | 5.8 | 6.1 | 7.1 |

EXAMPLE 12

Z and E isomers of (R,S) cyano-2-(6-phenoxypyridyl)-methyl (1R,cis) 2,2-dimethyl-3-[3-methylthio-propenyl]-cyclopropoane-carboxylate Using the procedure of Example 9, the ester derived from 3.4 g of (1R,cis) 2,2-dimethyl-3-[(ΔZ) carboxyethenyl]-cyclopropane-carboxylic acid and methylmercaptan were reacted to form after chromatography over silica gel and elution with an 8-2 hexane-ethyl acetate mixture 1.42 g of the Z isomer of (R,S) cyano-2-(6-phenoxypyridyl)-methyl (1R,cis) 2,2-dimethyl-3-[3-oxo-3-methylthio-propenyl]-cyclopropane-carboxylate with a specific rotation of $[\alpha]_D^{20} = +71.5° \pm 3°$ (c=0.5% in chloroform) and then 0.76 g of the E isomer with a specific rotation of $[\alpha]_D^{20} = -50.5° \pm 2°$ (c=0.5% in CHCl₃).

| Analysis: $C_{23}H_{22}N_2O_4S$: molecular weight = 422.506 | | | | |
|---|---|---|---|---|
| Calculated: | % C 65.38 | % H 5.25 | % N 6.63 | % S 7.59 |
| Found: Z isomer | 65.3 | 5.4 | 6.4 | 7.6 |
| E isomer | 65.3 | 5.5 | 6.4 | 7.6 |

EXAMPLE 13

(S) cyano-(3-phenoxy-4-fluorophenyl)-methyl (1R,cis) 2,2-dimethyl-3-[(ΔZ)3-oxo-3-methylthio-propenyl]-cyclopropane-carboxylate A solution of 1.73 g of methyl mercaptan in 4 ml of benzene was added to a mixture of 2.7 g of (1R,cis) 2,2-dimethyl-3-[(ΔZ) carboxyethenyl]-cyclopropane-carboxylic acid chloride prepared from the corresponding acid prepared by the process of Europe application No. 41,021, 15 ml of methylene chloride and 4 g of calcium carbonate and the mixture was stirred at 20° C. for 60 hours and was filtered. The filtrate was washed with aqueous monosodium phosphate solution and then with water, dried and evaporated to dryness. The residue was chromatographed over silica gel and was eluted with methylene chloride to obtain 1.3 g of (S) cyano-(3-phenoxy-4-fluorophenyl)-methyl (1R,cis) 2,2-dimethyl-3-[(ΔZ)-3-oxo-3-methylthio-propenyl]-cyclopropane-carboxylate with a melting point of 103° C. and a specific rotation of $[\alpha]_D^{20} = +55° \pm 2°$ (c=0.8% in benzene).

| Anzlysis: $C_{24}H_{22}IFNO_4S$; molecular weight = 439.510 | | | | | |
|---|---|---|---|---|---|
| Calculated: | % C 65.59 | % H 5.05 | % 3.19 | % S 7.30 | % F 4.32 |
| Found: | 65.7 | 5.0 | 3.2 | 7.1 | 4.4 |

EXAMPLE 14

(S) cyano-(3-phenoxy-4-fluoro-phenyl)-methyl (1R,cis) 2,2-dimethyl-3-[(ΔZ) 3-oxo-3-isopropylthio-propenyl]-cyclopropane-carboxylate Using the procedure of Example 5, 2.9 g of (S) cyano-(3-phenoxy-4-fluoro-phenyl)-methyl (1R,cis) 2,2-dimethyl-3-[(ΔZ)-carboxyethenyl]-cyclopropane-carboxylate prepared from the corresponding acid [process described in European application No. 41,021] and isopropylmercaptan were reacted to obtain after chromatography over silica gel and elution with an 8-2 hexane-ethyl acetate mixture 1.2 g of (S) cyano-(3-phenoxy-4-fluoro-phenyl)-methyl (1R,cis) 2,2-dimethyl-3[(ΔZ) 3-oxo-3-isopropylthio-propenyl]-cyclopropanecarboxylate melting at 64° C. and having a specific rotation of $[\alpha]_D^{20} = +55° \pm 2.5°$ (c=0.6% in benzene).

| Analysis: $C_{26}H_{26}FNO_4S$: molecular weight = 467.564 | | | | | |
|---|---|---|---|---|---|
| Calculated: | % C 66.79 | % H 5.60 | % F 4.06 | % N 3.00 | % S 6.86 |
| Found: | 67.1 | 5.6 | 4.3 | 3.0 | 6.9 |

EXAMPLE 15

(S) cyano-(3-phenoxy-4-fluoro-phenyl)-methyl (1R,cis) 2,2-dimethyl-3-[(ΔZ) 3-oxo-3-ethylthio-propenyl]-cyclopropanecarboxylate Using the procedure of Example 14, the said ester and ethylmercaptan were reacted to obtain (S) cyano-(3-phenoxy-4-fluoro-phenyl)-methyl (1R,cis) 2,2-dimethyl-3-[(ΔZ) 3-oxo-3-ethylthio-propenyl]-cyclopropane-carboxylate with a specific rotation of $[\alpha]_D^{20} = -58° \pm 2.5°$ (c=0.6% in benzene).

| Analysis: $C_{25}H_{24}FNO_4S$; molecular weight = 453.537 | | | | | |
|---|---|---|---|---|---|
| Calculated: | % C 66.21 | % H 5.33 | % N 3.09 | % F 4.19 | % S 7.07 |
| Found: | 66.2 | 5.3 | 3.0 | 4.5 | 7.0 |

EXAMPLE 16

Z and E isomers of (S) cyano-(3-phenoxy-4-fluoro-phenyl)-methyl (1R,cis) 2,2-dimethyl-3-[3-oxo-3-tert.-butylthiopropenyl]-cyclopropane-carboxylate Using the procedure of Example 14, the ester derived from 2.7 g of the acid and tert.-butylmercaptan were reacted to obtain 0.61 g of the Z isomer of (S) cyano-(3-phenoxy-4-fluoro-phenyl)-methyl (1R,cis) 2,2-dimethyl-3-[3-oxo-3-tert.-butylthio-propenyl]-cyclopropane-carboxylate melting at 96° C. and having a specific rotation of $[\alpha]_D^{20} = +63.5° \pm 2.5°$ (c=0.75% in benzene) and 3.4 g of the corresponding E isomer melting at 122° C. and having a specific rotation of $[\alpha]_D^{20} = +61.5° \pm 2.5°$ (c=0.5% in benzene).

| Analysis: $C_{27}H_{28}FNO_4S$; molecular weight = 481.591 | | | | | |
|---|---|---|---|---|---|
| Calculated: | 67.34 | % H 5.86 | % F 3.94 | % N 2.91 | % S 6.66 |
| Found: | | | | | |
| Z isomer | 67.5 | 5.9 | 3.9 | 2.8 | 6.6 |
| E isomer | 67.4 | 5.8 | 4.1 | 2.8 | 6.4 |

EXAMPLE 17

(1S) 2-methyl-4-oxo-3-(2-propenyl)-2-cyclopenten-1-yl (1R,cis) 2,2-dimethyl-3-[(ΔZ) 3-oxo-3-methylthio-propenyl]-cyclopropane-carboxylate A solution of 260 mg of 4-dimethylamino-pyridine, 1.7 g of dicyclohexylcarbodiimide and 10 ml of methylene chloride was added at 0° to 5° C. to a mixture of 473 mg of methylmercaptan, 2.6 g of (1S) 2-methyl-4-oxo-3-(2-propenyl)-2-cyclopenten-1-yl (1R,cis) 2,2-dimethyl-3-[(ΔZ)-carboxyethenyl]-cyclopropane-carboxylate and 26 ml of methylene chloride and the mixture was stirred at 0° to 5° C. for 10 minutes, at 20° C. for one hour and was filtered. The filtrate was washed with 1N hydrochloric acid and then with water, dried and evaporated to dryness. The 2.6 g of residue were chromatographed over silica gel and were eluted with an 8-2 hexane-ethyl acetate mixture to obtain 1.5 g of (1S) 2-methyl-4-oxo-3-(2-propenyl)-2-cyclopenten-1-yl (1R,cis) 2,2-dimethyl-3-[(ΔZ) 3-oxo-3-methylthio-propenyl]-cyclopropane-carboxylate with a specific rotation of $[\alpha]_D^{20} = +97° \pm 2.5°$ (c=0.5% in chloroform).

| Analysis: $C_{17}H_{24}O_4S$; molecular weight = 348.465 | | | |
|---|---|---|---|
| Calculated: | % C 65.49 | % H 6.94 | % S 9.20 |
| Found: | 65.8 | 7.0 | 9.2 |

EXAMPLE 18

(1S) 2-methyl-4-oxo-3-(2-propenyl)-2-cyclopenten-1-yl (1R,cis) 2,2-dimethyl-3-[(ΔZ) 3-oxo-3-ethylthio-propenyl]-cyclopropane-carboxylate Using the procedure of Example 17, the ester derived from 2.5 g of the corresponding acid and ethylmercaptan were reacted to obtain 1.055 g of (1S) 2-methyl-4-oxo-3-(2-propenyl)-2-cyclopenten-1-yl (1R,cis) 2,2-dimethyl-3-[(ΔZ) 3-oxo-3-ethylthio-propenyl]-cyclopropane-carboxylate with a specific rotation of $[\alpha]_D^{20} = +91° \pm 1.5°$ (c=1.2% in chloroform).

| Analysis: $C_{20}HL_{20}OL_4S$; molecular weight = 362.492 | | | |
|---|---|---|---|
| Calculated: | % C 66.37 | % H 7.23 | % S 8.85 |
| Found: | 66.4 | 7.4 | 8.6 |

EXAMPLE 19

Z and E isomers of 3-phenoxy-benzyl (1R,cis) 2,2-dimethyl-3-[3-oxo-3-isopropylthio-propenyl]-cyclopropane-carboxylate 1 ml of isopropylmercaptan, 25 mg of 4-dimethylamino-pyridine and a solution of 1.41 g of dicyclohexylcarbodiimide in 10 ml of methylene chloride were added at 5° C. to a mixture of 2.5 g of 3-phenoxy-benzyl (1R,cis) 2,2-dimethyl-3-[(ΔZ) carboxyethenyl]-cyclopropane-carboxylate and 10 ml of methylene chloride and the mixture was stirred at 10° C. for 10 minutes and at 20° C. for 4 hours and was filtered. The filtrate was washed with water, dried and evaporated to dryness. The residue was chromatographed over silica gel and was eluted with an 85–15 hexane-ethyl acetate mixture to obtain 1.413 g of the Z isomer of 3-phenoxy benzyl (1R,cis) 2,2-dimethyl-3-[3-oxo-3-isopropylthio-propenyl]-cyclopropane-carboxylate with a specific rotation of $[\alpha]_D^{20} = +65° \pm 1.5°$ (c=0.7% in chloroform) and 1.003 g of the E isomer with a specific rotation of $[\alpha]_D^{20} = -62° \pm 2.5°$ (c=0.5% in chloroform).

| Analysis: $C_{25}H_{28}O_4S$; molecular weight = 424.564 | | | |
|---|---|---|---|
| Calculated: | % C 70.73 | % H 6.65 | % S 7.55 |
| Found: Z isomer | 71.0 | 6.8 | 7.6 |
| E isomer | 71.0 | 6.8 | 74 |

EXAMPLE 20

3-Phenoxy-benzyl (1R,cis) 2,2-dimethyl-3-[(ΔZ) 3-oxo-3-ethylthio-propenyl]-cyclopropane-carboxylate Using the procedure of Example 19, the ester derived from 2.5 g of the corresponding acid and ethylmercaptan were reacted to obtain 2.14 g of 3-phenoxy-benzyl (1R,cis) 2,2-dimethyl-3-[(ΔZ) 3-oxo-3-ethylthio-propenyl]-cyclopropanecarboxylate with a specific rotation of $[\alpha]_D^{20} = +64.5° \pm 2.5°$ (c=0.5% in chloroform).

| Analysis: $C_{24}H_{26}O_4S$; molecular weight = 410.536 | | | |
|---|---|---|---|
| Calculated: | % C 70.22 | % H 6.38 | % S 7.81 |
| Found: | 70.5 | 6.4 | 7.7 |

EXAMPLE 21

3-phenoxy-benzyl (1R,cis) 2,2-dimethyl-3-[(ΔZ) 3-oxo-3-methylthio-propenyl]-cyclopropane-carboxylate Using the procedure of Example 19, the ester derived from 2.1 g of the corresponding acid and methylmercaptan were reacted to obtain 1.82 g of 3-phenoxy-benzyl (1R,cis) 2,2-dimethyl-3-[(ΔZ) 3-oxo-3-methylthio-propenyl]-cyclopropanecarboxylate with a specific rotation of $[\alpha]_D^{20} = +60.5° \pm 3°$ (c=0.7% in chloroform).

| Analysis: $C_{23}H_{24}O_4S$; molecular weight = 396.509 | | | |
|---|---|---|---|
| Calculated: | % C 69.67 | % H 6.10 | % S 8.09 |
| Found: | 69.6 | 6.1 | 7.8 |

EXAMPLE 22

Z and E isomers of 3-phenoxy-benzyl (1R,cis) 2,2-dimethyl-3-[3-oxo-3-tert.-butylthio-propenyl]-cyclopropane-carboxylate Using the procedure of Example 19, the ester derived from 2.5 g of the corresponding acid and tert.-butylmercaptan were reacted to obtain 0.2 g of the Z isomer of 3-phenoxy-benzyl (1R,cis) 2,2-dimethyl-3-[3-oxo-3-tert.-butylthio-propenyl]-cyclopropane-carboxylate with a specific rotation of $[\alpha]_D^{20} = +73° \pm 3°$ (c=0.5% in chloroform) and 0.7 g of the corresponding E isomer with a specific rotation of $[\alpha]_D^{20} = -65° \pm 2.5°$ (c=0.5% in chloroform).

| Analysis: $C_{26}H_{30}SO_4$; molecular weight = 438.591 | | | |
|---|---|---|---|
| Calculated: | % C 71.20 | % H 6.89 | % S 7.31 |
| Found: Z isomer | 71.3 | 7.1 | 7.5 |
| E isomer | 70.7 | 7.0 | 6.9 |

EXAMPLE 23

Z and E isomers of (R)α-(3-phenoxyphenyl)-ethyl (1R,cis) 2,2-dimethyl-3-[3-oxo-3-tert.-butylthio-propenyl]-cyclopropanecarboxylate Using the procedure of Example 19, 3 g of (R) α-(3-phenoxyphenyl)-ethyl (1R,cis) 2,2-dimethyl-3-[(ΔZ)carboxyethenyl]cyclopropane-carboxylate and tert.-butylmercaptan were reacted to obtain after chromatography over silica gel and elution with a 95-5 hexane-ethyl acetate mixture 0.97 g of the Z isomer of (R) α-(3-phenoxyphenyl)ethyl (1R,cis) 2,2-dimethyl-3-[3-oxo-3-tert.-butylthio-propenyl]-cyclopropane-carboxylate with a specific rotation of $[\alpha]_D^{20} = +134° \pm 3.5°$ (c=0.65% in chloroform) and 1.10 g of the corresponding E isomer with a specific rotation of $[\alpha]_D^{20} = +44.5° \pm 1.5°$ (c=0.85% in chloroform).

| Analysis: $C_{27}H_{32}O_4S$: molecular weight = 452.618 | | | |
|---|---|---|---|
| Calculated: | % C 71.65 | % H 7.13 | % S 7.08 |

-continued

| Analysis: $C_{27}H_{32}O_4S$: molecular weight = 452.618 | | | |
|---|---|---|---|
| Found: Z isomer | 71.5 | 7.2 | 7.1 |
| E isomer | 71.3 | 7.2 | 7.0 |

EXAMPLE 24

Z and E isomers of 3-phenoxy-4-fluoro-benzyl (1R,cis) 2,2-dimethyl-3-[3-oxo-3-tert.-butylthio-propenyl]-cyclopropanecarboxylate Using the procedure of Example 19, 9.7 g of 3-phenoxy-4-fluoro-benzyl (1R,cis) 2,2-dimethyl-3-[(ΔZ) carboxyethenyl]-cyclopropane-carboxylate and tert.-butylmercaptan were reacted to obtain after chromatography over silica gel and elution with a 95-5 hexane-ethyl acetate mixture 1.96 g of the Z isomer of 3-phenoxy-4-fluorobenzyl (1R,cis) 2,2-dimethyl-3-[3-oxo-3-tert.-butylthiopropenyl]-cyclopropane-carboxylate with a specific rotation of $[\alpha]_D^{20} = +80.5° \pm 3°$ (c=0.5% in chloroform) and 8.5 g of the corresponding E isomer with a specific rotation of $[\alpha]_D^{20} = -62° \pm 2.5°$ (c=0.6% in chloroform) and having a melting point of 82° C.

| Analysis: $C_{26}H_{29}FO_4S$; molecular weight = 456.581 | | | | |
|---|---|---|---|---|
| Calculated: | % C 68.40 | % H 6.40 | % F 4.16 | % S 7.02 |
| Found Z isomer | 68.5 | 6.6 | 4.1 | 7.1 |
| E isomer | 68.4 | 6.6 | 4.1 | 7.1 |

EXAMPLE 25

Pentafluorobenzyl (1R,cis) 2,2-dimethyl-3-[(ΔZ) 3-oxo-3-methylthio-propenyl]-cyclopropane-carboxylate Using the procedure of Example 19, 2.6 g of pentafluorobenzyl (1R,cis) 2,2-dimethyl-3-[(ΔZ) carboxyethenyl]-cyclopropane-carboxylate and methylmercaptan were reacted to obtain after chromatography over silica gel and elution with a 95-5 hexane-ethyl acetate mixture 1.9 g of pentafluorobenzyl (1R,cis) 2,2-dimethyl-3-[(ΔZ) 3-oxo-3-methylthio-propenyl]-cyclopropane-carboxylate melting at 45° C. and having a specific rotation of $[\alpha]_D^{20} = +36° \pm 1.5°$ (c=1% in chloroform).

| Analysis: $C_{17}H_{15}F_4OL_3S$; molecular weight = 394.364 | | | | |
|---|---|---|---|---|
| Calculated: | % C 51.78 | % H 3.83 | % F 24.09 | % S 8.13 |
| Found: | 51.9 | 4.0 | 24.4 | 8.4 |

EXAMPLE 26

A wettable powder was prepared by homogenously mixing 15% by weight of the Z isomer of example 1, 10% by weight of Ekapersol S (condensation product of sodium naphtalene sulfonate), 0.5% by weight of Brecolane N V A (sodium alkyl naphtalene sulfonate), 34.5% by weight of Zeosil 39 (precipitated synthetic hydrated silica) and 40% by weight of Vercoryl S (colloidal Kaolin).

An emulsifiable concentrate was prepared by intimately mixing 0.015 g of the Z isomer of Example 1, 0.5 g of piperonyl butoxide, 0.1 g of Topanol A, 3.5 g of Tween 80 and 95.885 of xylene.

A second emulsifiable concentrate was prepared by intimately mixing 45 g of the Z isomer of Example 1, 6.4 g of Atlox 4851 (mixture of alkyl arylsulfonates and polyoxyethylene triglycerides with a viscosity of 300 to 700 cps at 25° C.), 3.2 g of Atlox 4855 (mixture of alkyl arylsulfonates and polyoxyethylene triglycerides with a viscosity of 1500–1900 cps at 25° C.) and 45.4 g of xylene.

An emulsifiable concentrate was prepared containing 20% by weight of the Z isomer of Example 1, 6.4% by weight of Atlox 4851, 3.2% by weight of Atlox 4855 and 70.4% by weight of xylene.

A fumigant composition was prepared by homogenously mixing 0.25 g of the product of Example 6, 25 g of Tabu powder, 40 g of cedar needle powder, 33.75 g of pine wood powder, 0.5 g of brilliant green and 0.5 g of p-nitrophenol.

PARASITIC STUDY

A. Lethal effect on houseflies

The test insects were female houseflies of strain sensitive to pyrethrinoids, bred at 22°–23° C. and 60 to 65% relative humidity and 4 to 5 days old. One $\mu l$ of an acetone solution of the test compound was topically applied to the dorsal thorax of the insects with an Arnold micro-manipulator using 50 insects for each dose. The number of dead was determined 24 hours later and the $LD_{50}$ dose in nanograms (the dose killing 50% of the insects) was determined. The results are reported in table I.

TABLE I

| Compound of Example | $LD_{50}$ in nanograms |
|---|---|
| E isomer - 1 | 35.0 |
| Z isomer - 3 | 1.28 |
| E isomer - 3 | 58.3 |
| Z isomer - 2 | 0.98 |
| Z isomer - 4 | 5.1 |

The tested products showed a lethal activity against houseflies.

B. Lethal effect on larvae of Spodoptera littoralis

The test was effected by a topical application of an acetone solution of the test compound with an Arnold micromanipulator to the dorsal thorax of larvae of Spodoptera littoralis in the 4th larvae stage using 15 insects per dose. The larvae were 10 days old having been kept at 24° C. and a 65% relative humidity and the larvae, after treatment, were placed in an artifical nutritive medium (Poitout media) and the number of dead was determined after 48 hours. The results are reported in Table II.

TABLE II

| Compound of Example | isomer | $LD_{50}$ in nanograms |
|---|---|---|
| 1 | Z | 40.0 |
| 1 | E | 77.3 |
| 3 | Z | 52.9 |
| 2 | Z | 29.8 |

The test showed that the products had a lethal activity against larvae of Spodoptera littoralis.

C. Knock-down power against houseflies 50 female houseflies 4 to 5 days old per dose were subjected to a direct spray in a Kearns and March cylinder using as the solvent a mixture in equal volumes of acetone and Isopar L (petroleum solvent), using an amount of solution of 2×0.2 cm3). About 50 individuals per dose of treatment are used. Readings were taken every minute for 10 minutes and then at 15 minutes to determine the $KT_{50}$ by the usual method. The results are reported in table III.

TABLE III

| Compound of Example | isomer | $KT_{50}$ in min |
|---|---|---|
| 1 | Z | 3.1 |
| 1 | E | 4.9 |
| 3 | Z | 5.4 |
| 3 | E | 2.8 |
| 2 | Z | 3.7 |

The test showed that the compounds had a knockdown activity against houseflies.

D. Activity against Acanthocelida Sobtectus

The test was effected by a topical application of 1 $\mu l$ of an acetone solution of the test compound to the thorax of the insect. The $LD_{50}$ was determined per insect and expressed in nanograms. The results are reported in table IV.

TABLE IV

| Compound of Example | isomer | $LD_{50}$ in ng |
|---|---|---|
| 1 | Z | 7.5 |
| 3 | Z | 13.0 |
| 2 | Z | 17.7 |
| 4 | Z | 32.6 |

The results showed that the compounds had an activity against Acanthocelida sobtectus.

E. Activity against Germanic beetles

Tests with the compounds of the example were carried out on Blatella germanic beetles with an acetone solution of a predetermined concentration of the compound being placed in a Petri dish with a 20 cm diameter. After evaporation of the acetone, 26 male beetles per test concentration were placed in the Petri dish for one hour and the insects were then placed in healthly surroundings. The number of dead beetles was determined after 24 hours, 48 hours and 3 and 5 days and the lethal concentration at which 50% of the beetles ($LC_{50}$) were dead was determined and is reported in Table V.

TABLE V

| Compound of Example | isomer | $LC_{50}$ in mg/m² |
|---|---|---|
| 1 | Z | 0.25 |
| 3 | Z | 0.21 |
| 2 | Z | 0.18 |
| 4 | Z | 0.17 |

The results showed that the compounds had a lethal activity against Germanica beetles.

F. Activity Against Tetranychus urticae

Bean plants with two cotyledonary leaves were treated with a Fischer pistol with an acetone solution of the test compounds and after drying, 25 female Tetranychus urticae acariens were placed on each leaf that is 50 individuals per test. Readings of control were determined after 1, 24, 48 and 72 hours of contact and the compounds of Examples 1 to 8 all showed a good acaricidal activity against *Tetranychus urticae.*

G. Activity Against *Panagrellus silusiae*

About 2000 nematodes suspended in 0.5 ml of water were placed in a 50 ml receptacle and 10 ml of an aqueous solution of the test compound at a dose of 1 or 0.1 g/l were added thereto. 3 tests were run for each concentration and after 24 hours, the aqueous media was homogenized and the number of living and dead nematodes in 1 ml thereof was determined with a Peter slide and the results were compared to untreated controls. The compounds of Examples 1 to 8 showed a nematocidal activity against *Panagrellus silusiae.*

Various modifications of the compounds and methods of the invention may be made without departing from the spirit or scope thereof and it is to be understood that the invention is intended to be limited only as defined in the appended claims.

What we claim is:

1. A compound selected from the group consisting of stereoisomeric forms and mixtures thereof of compounds of the formula

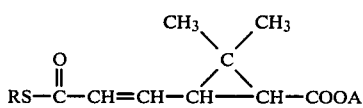

wherein R is selected from the group consisting of phenyl optionally substituted with at least one member of the group consisting of —OH, alkyl and alkoxy of 1 to 8 carbon atoms, —CF$_3$, —OCF$_3$, —SCF$_3$, —Cl, Br and F, optionally unsaturated cycloalkyl of 3 to 7 carbon atoms optionally substituted on the cycloalkyl with at least one member of the group consisting of halogen, alkyl of 1 to 6 carbon atoms, alkoxy of 1 to 6 carbon atoms and —NO$_2$, and alkyl of 1 to 18 carbon atoms and alkenyl and alkynyl of 2 to 18 carbon atoms optionally substituted with at least one member of the group consisting of halogen, —OH, —SH, —OR′ and —SR′ and R′ is selected from the group consisting of alkyl of 1 to 8 carbon atoms, —NO$_2$, —CN, —SO$_3$H, —PO$_4$H$_2$,

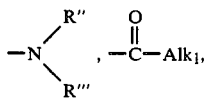

—SO$_2$Alk$_2$ and SO$_2$Alk$_3$, R″ and R‴ are individually selected from the group consisting of hydrogen and alkyl of 1 to 8 carbon atoms and Alk$_1$, Alk$_2$ and Alk$_3$ are alkyl of 1 to 18 carbon atoms or benzyl or phenethyl optionally substituted with at least one member of the group consisting of —OH, alkyl and alkoxy of 1 to 8 carbon atoms, halogens, —CF$_3$, —OCF$_3$, —SCF$_3$ and

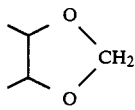

(G), or alkyl substituted on two adjacent carbon atoms with the group

(G$_1$) or substituted with

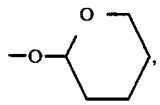

A is selected from the the group consisting of

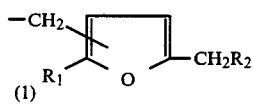

wherein R$_1$ is selected from the group consisting of hydrogen and methyl and R$_2$ is selected from the group consisting of —CH$_2$—C≡CH and phenyl,

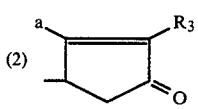

wherein a is selected from the group consisting of hydrogen and methyl and R$_3$ is an aliphatic group of 2 to 6 carbon atoms containing at least one carbon-carbon unsaturation,

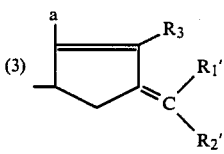

wherein a is selected from the group consisting of hydrogen and methyl and R$_3$ has the above definition and R$_1$′ and R$_2$′ are individually selected from the group consisting of hydrogen, halogen, alkyl of 1 to 6 carbon atoms, phenyl, cyano and alkoxy-carbonyl of 2 to 5 carbon atoms,

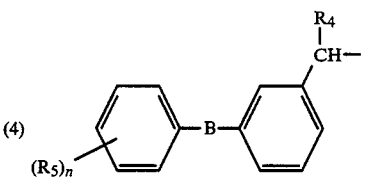

wherein B is selected from the group consisting of —CH$_2$—,

—O— and —S—, R$_4$ is selected from the group consisting of hydrogen, —CN, —CH$_3$, —CONH$_2$, —CSNH$_2$, and —C≡CH, R$_5$ is selected from the group consisting of halogen and —CH$_3$ and n is an integer from 0, 1 or 2

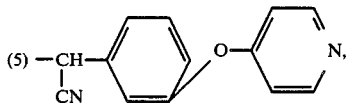

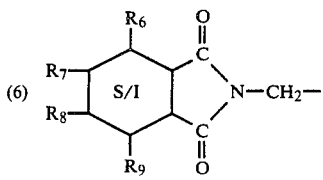

wherein R$_6$, R$_7$, R$_8$ and R$_9$ are selected from the group consisting of hydrogen, chlorine and methyl and S/I symbolizes an aromatic ring or dihydro or tetrahydro ring,

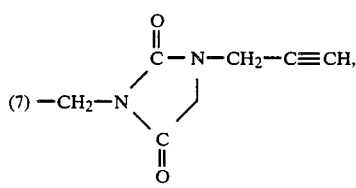

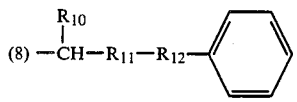

wherein R$_{10}$ is selected from the group consisting of hydrogen and —CN, R$_{12}$ is selected from the group consisting of —CH$_2$— and —O— and R$_{11}$ is selected from the group consisting of thiazolyl and thiadiazolyl with the bond to

being in one of the positions so that there is a carbon atom wherein R$_{11}$ and R$_{12}$ are connected between a sulfur atom and a nitrogen atom,

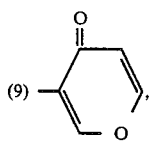

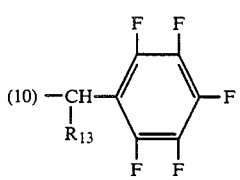

wherein R$_{13}$ is selected from the group consisting of hydrogen and —CN

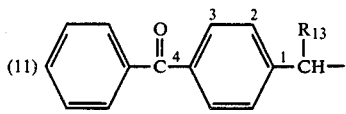

wherein R$_{13}$ has the above definition and the benzoyl is in the 4-position,

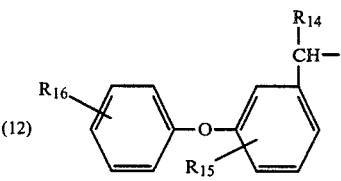

wherein R$_{14}$ is selected from the group consisting of hydrogen, methyl, ethynyl and —CN and R$_{15}$ is selected from the group consisting of fluorine, chlorine and bromine and R$_{16}$ is selected from the group consisting of hydrogen, bromine, chlorine and fluorine and

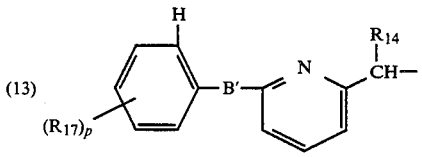

wherein R$_{14}$ has the above definition, p is 0, 1 or 2, each R$_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, and fluorine, B' is selected from the group consisting of —O—, and —S— and the double bond in the 1'-position of the 3-lateral side change has Z or E geometry.

2. A compound of claim 1 wherein the double bond has the Z geometry.

3. A compound of claim 1 or 2 wherein the cyclopropane carboxylic acid moiety has the (1R,cis) or (1R,trans) structure.

4. A compound of claim 1 or 2 wherein the cyclopropane carboxylic acid moiety has the (1R,cis) structure.

5. A compound of claim 1 or 2 wherein A is α-cyano-3-phenoxy-benzyl in the (S), (R) or (R,S) form.

6. A compound of claim 1 or 2 wherein A is [3-(propyn-2-yl)-2,5-dioxo-imidazolidinyl]methyl.

7. A compound of claim 1 or 2 wherein R is alkyl of 1 to 18 carbon atoms.

8. A compound of claim 1 wherein R is methyl, ethyl, isopropyl or tert.-butyl.

9. An insecticidal composition comprising an insecticidally effective amount of at least one compound of claim 1 and an inert carrier.

10. A composition of claim 9 wherein the double bond has the Z geometry.

11. A composition of claim 9 wherein the cyclopropane-carboxylic acid moiety has the (1R,cis) or (1R,trans) structure.

12. A composition of claim 9 wherein the cyclopropane carboxylic acid moiety has the (1R,cis) structure.

13. A composition of claim 9 wherein A is α-cyano-3-phenoxy-benzyl in the (S), (R) or (R,S) form.

14. A composition of claim 9 wherein A is [3-propyn-2-yl)-2,5-dioxo-imidazolidinyl]methyl.

15. A composition of claim 9 wherein R is alkyl of 1 to 18 carbon atoms.

16. A composition of claim 9 wherein R is methyl, ethyl, isopropyl or tert.-butyl.

17. A method of combatting insects comprising contacting insects with an insecticidally effective amount of at least one compound of claim 1.

18. A method of claim 17 wherein the double bond has the Z geometry.

19. A method of claim 17 wherein the cyclopropane carboxylic acid moiety has the (1R,cis) or (1R,trans) structure.

20. A method of claim 17 wherein the cyclopropane carboxylic acid moiety has the (1R,cis) structure.

21. A method of claim 17 wherein A is α-cyano-3-phenoxy-benzyl in the (S), (R) or (R,S) form.

22. A method of claim 17 wherein A is [3-(propyn-2-yl)-2,5-dioxo-imidazolidinyl]methyl.

23. A method of claim 17 wherein R is alkyl of 1 to 18 carbon atoms.

24. A method of claim 17 wherein R is methyl, ethyl, isopropyl or tert.-butyl.

25. An acaricidal composition comprising an acaricidally effective amount of at least one compound of claim 1 and an inert carrier.

26. A method of combatting acariens comprising contacting acariens with an acaricidally effective amount of at least one compound of claim 1.

27. A nematocidal composition comprising a nematocidally effective amount of at least one compound of claim 1 and an inert carrier.

28. A method of combatting nematodes comprising contacting nematodes with an nematocidally effective amount of at least one compound of claim 1.

29. An animal feed containing an acaricidally effective amount of at least one compound of claim 1.

* * * * *